US006126810A

United States Patent [19]

Fricker et al.

[11] Patent Number: 6,126,810

[45] **Date of Patent: *Oct. 3, 2000**

[54] GENERATION OF ACTIVE CHLORINE IN THE PRESENCE OF AN ORGANIC LOAD FROM SODIUM CHLORIDE IN WATER

[75] Inventors: Christopher M. Fricker, Concord; Paul S. Malchesky, Painesville Township; Brian C. Wojcieck, Willoughby; Jason M. Sell, Seven Hills, all of Ohio

[73] Assignee: Steris Corporation, Mentor, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 09/067,278

[22] Filed: Apr. 27, 1998

[51] Int. Cl.[7] .......... C02F 1/46

[52] U.S. Cl. .......... 205/500; 205/556; 205/701; 205/746; 205/748; 204/228.6; 204/257; 204/263; 204/264; 204/275.1

[58] Field of Search .......... 204/228.6, 257, 204/263, 264, 275, 276; 205/701, 556, 500, 746, 747

[56] References Cited

U.S. PATENT DOCUMENTS

| | | | |
|---|---|---|---|
| 3,616,355 | 10/1971 | Themy et al. | 205/701 |
| 4,172,773 | 10/1979 | Pellegri et al. . | |
| 4,510,026 | 4/1985 | Spaziante . | |
| 4,519,889 | 5/1985 | Pellegri et al. . | |
| 4,560,455 | 12/1985 | Porta et al. | 205/701 |
| 4,710,233 | 12/1987 | Hohmann et al. | 205/701 |
| 4,714,534 | 12/1987 | Fair et al. . | |
| 4,839,004 | 6/1989 | Castellini | 205/701 |
| 5,250,160 | 10/1993 | Oksman et al. . | |
| 5,385,650 | 1/1995 | Howarth et al. . | |
| 5,759,489 | 6/1998 | Miura et al. | 205/746 |
| 5,932,171 | 8/1999 | Malchesky | 422/29 |

FOREIGN PATENT DOCUMENTS

| | | |
|---|---|---|
| 0761235 | 3/1997 | European Pat. Off. . |
| 3121336 A1 | 12/1982 | Germany . |
| 3430631 A1 | 2/1986 | Germany . |
| 7171101 | 11/1995 | Japan . |
| WO 99/08719 | 2/1999 | WIPO . |

*Primary Examiner*—Arun S. Phasge
*Attorney, Agent, or Firm*—Fay, Sharpe, Fagan, Minnich & McKee, LLP

[57] ABSTRACT

A recirculation system for electrochemically activated antimicrobial solutions returns antimicrobial solution which has been depleted of active antimicrobial species to a electrolytic cell for regeneration of the active species. Organic load, which frequently contaminates items to be sterilized or disinfected, such as medical instruments, rapidly depletes the active antimicrobial species in a conventional treatment system, reducing the effectiveness of microbial decontamination by electrochemically activated solutions. By recirculating the antimicrobial through the electrolytic cell, the concentration of active species is maintained at a level at which efficient sterilization is achieved.

26 Claims, 1 Drawing Sheet

CATHOLYTE
30
10
16
18
14
$H_2O$
38
12
36
20
34
40
FREE CHLORINE
28
NaCl
24
26
22

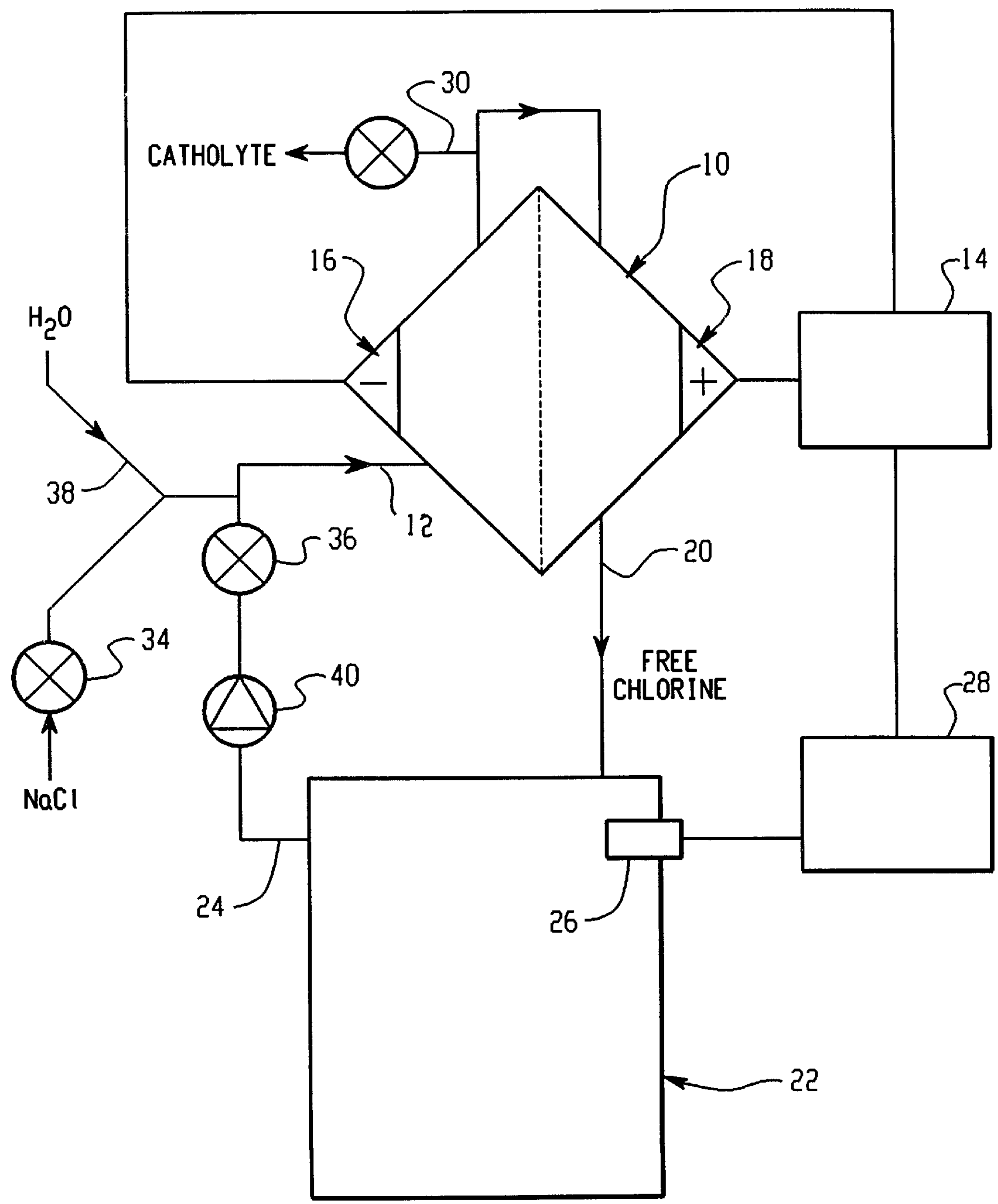
30
CATHOLYTE
10
16
18
14
$H_2O$
38
12
36
20
34
40
FREE
CHLORINE
28
NaCl
24
26
22

GENERATION OF ACTIVE CHLORINE IN THE PRESENCE OF AN ORGANIC LOAD FROM SODIUM CHLORIDE IN WATER

BACKGROUND OF THE INVENTION

The present invention relates to the sterilization and disinfection arts. It finds particular application in conjunction with electrochemically activated solutions containing chlorine species for sterilization or disinfection of medical and pharmaceutical equipment in the presence of organic contamination, and will be described with particular reference thereto. It should be appreciated, however, that the invention is also applicable to other sterilization, disinfection, and sanitization methods employing oxidizing species in which the active species is degraded over time.

The reusability of medical instruments has become increasingly important in an effort to provide cost effective health care. Recently, electrochemically activated antimicrobial solutions produced from brine have been developed for disinfection or sterilization of medical instruments and the like. The species active as antimicrobials, such as hypochlorite and other chlorine species, which are often referred to as "free" chlorine, are generated by passing brine (a solution of sodium chloride in water) through a specialized electrochemical cell. Typically, free chlorine concentrations of from about 2 to about 2000 ppm are employed for disinfection or sterilization. The instruments are treated by immersing them for a predetermined period in the activated solution. These solutions have the advantage of effecting fairly rapid microbial decontamination without leaving harmful or unsightly deposits on the instruments. Moreover, the antimicrobial is advantageously generated only as it is required, avoiding the need for storing potentially hazardous oxidants.

Typically, instruments are cleaned with detergent, or the like, to remove dirt and other contaminants present, before disinfection or sterilization of the instruments in the electrochemically activated solution. However, organic contaminants, such as serum, which are deposited on the instruments during use or contaminants present in the cleaning water, are not always completely removed during this cleaning process. Many of the instruments which are now disinfected or sterilized, such as endoscopes, contain tortuous paths, narrow lumens, and other difficult to clean areas where organic material is sometimes trapped during the initial cleaning process.

Organic materials have now been found to render electrochemically active solutions inactive by reducing the concentration of active species available for oxidation. There remains a need for a method of regaining the activity of electrochemically activated solutions in the presence of organic materials.

The present invention provides a new and improved composition for use in electrochemically activated solutions which overcomes the above referenced problems and others.

SUMMARY OF THE INVENTION

In accordance with one aspect of the present invention, a method of liquid sterilization or disinfection of items in the presence of organic load is provided. The method comprises passing an amount of a halide solution through an electrolytic cell to generate an antimicrobial solution which includes active oxidizing species and transporting the antimicrobial solution to a treatment vessel. The method further comprises immersing items to be microbially decontaminated in the antimicrobial solution and returning a portion of the solution with depleted active oxidizing species from the vessel back to the electrolytic cell for generation of a regenerated antimicrobial solution which includes active oxidizing species.

In accordance with another aspect of the present invention, a method of regeneration of an electrochemically activated sterilizing or disinfecting solution is provided. The method comprises passing an amount of a first solution through an electrolytic cell to generate an antimicrobial solution which includes active oxidizing species and transporting the antimicrobial solution to a treatment vessel. The method further comprises immersing items to be microbially decontaminated in the antimicrobial solution. The method is characterized by returning a portion of the solution with depleted active oxidizing species from the vessel back to the electrolytic cell for generation of a regenerated antimicrobial solution which includes active oxidizing species.

In accordance with another aspect of the present invention, a system for regeneration of active species is provided. The system comprises a source of a salt solution and an electrolytic cell for generating an antimicrobial solution, which includes active antimicrobial species, from the salt solution and from a depleted solution which is depleted of active antimicrobial species. An inlet line fluidly connects the source of the salt solution to the electrolytic cell and an outlet line fluidly connects the electrolytic cell to the vessel for transporting the antimicrobial solution to the vessel. A return line fluidly connects the vessel to the electrolytic cell for returning a portion of the depleted antimicrobial solution to the electrolytic cell for regeneration of active antimicrobial species.

One advantage of the present invention is that it enables medical instruments to be microbially decontaminated in electrochemically activated solutions in the presence of organic load or degraded active species.

Another advantage of the present invention is that antimicrobial solution is regenerated, allowing it to be reused.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

The FIGURE is a schematic diagram of a preferred embodiment of a circulation system for regenerating active antimicrobial species of the present invention.

DETAILED DESCRIPTION OF THE PREFERRED EMBODIMENTS

With reference to the FIGURE, a circulation system provides for regeneration of a depleted active antimicrobial species. The system includes an electrochemically activated solution generator or electrolytic cell, such as an electrolytic chlorinator, 10. A first solution, such as brine, is passed into the generator through an inlet line 12. A voltage generator 14 applies a voltage across electrodes 16 and 18 within the generator. Electrode 16 is preferably an anode and is situated adjacent inlet line 12. Electrode 18 is preferably a cathode. Active antimicrobial species are thereby generated electrochemically in the first solution.

When the active species are to be used for sterilization or disinfection of medical instruments, they are then carried, as an antimicrobial solution, from the generator by an outlet line 20 to a sterilization or disinfection treatment vessel 22 containing the instruments. The rate of sterilization or disinfection is dependent on the period of exposure and the concentration of active halide species or other active oxidizing species. It has been found that an organic load, such as serum, present as a contaminant on the instruments, or in the water, rapidly depletes the active species in the antimicrobial solution, reducing the effectiveness of disinfection or sterilization. In addition, the active species may degrade due to the conditions of the solution, such as temperature, pH, or flow.

The active species are preferably regenerated by recirculating the partially depleted antimicrobial solution through the generator 10. A return line 24 carries the depleted antimicrobial solution from the treatment vessel 22 to the generator. Preferably, the return line directs the depleted antimicrobial solution to the generator through the inlet line 12. The generator generates a regenerated antimicrobial solution from the depleted antimicrobial solution which contains a higher concentration of active antimicrobial species than is present in the incoming depleted antimicrobial solution. Alternatively, a second generator is used for regeneration of the depleted antimicrobial solution. The regenerated solution is then carried by the outlet line 20 to the treatment vessel 22.

By recirculating the antimicrobial solution in this way, concentrations of active sterilant species sufficient for sterilization or disinfection are regained in the presence of an organic load in a brief period of time, preferably in a few minutes. Table 1 shows the effect of recirculation on a 0.1% sodium chloride solution in the presence of 1% bovine serum at 20° C. Even at this fairly high level of organic load, a free (active) chlorine concentration of over 180 ppm was achieved in 20 minutes of recirculation. Clearly, however, the time required for regeneration is also dependent, to some degree, on the volume of antimicrobial solution in the vessel 22, on the flow rate of the solution, and on the temperature. For smaller solution volumes typically employed in smaller instrument disinfectors or sterilizers, a shorter regeneration time is to be expected.

TABLE 1

Effect of Recirculation at 801/Hr. Following Addition of 1% Bovine Serum to 31 of 0.1% Sodium Chloride Solution at 20° C.

| Recirculation Time (min.) | Free Chlorine (ppm) |
|---|---|
| 2 | 13 |
| 5 | 34 |
| 10 | 69 |
| 15 | 130 |
| 20 | 182 |

In practice, much lower organic material contamination levels are anticipated. Table 2 shows the effect of different concentrations of bovine serum on the free chlorine concentration in electrochemically activated solutions generated from sodium chloride at 20° C. At high serum concentrations (above 1% bovine serum) it was found that little or no measurable free chlorine was detected. At serum concentrations below 1%, the measured free chlorine was higher, allowing for a more rapid rise in the concentration of active species.

TABLE 2

Effect of Bovine Serum on Free Chlorine Concentration in Electrochemically Activated Solutions Generated from 10% Sodium Chloride at 20° C. in a Non-Recirculated Solution

| % Serum | Free Chlorine (ppm) |
|---|---|
| 0 | 304 |
| 0.1 | 251 |
| 0.5 | 106 |
| 1.0 | 10 |

Preferably, the antimicrobial solution is recirculated continuously through the generator and a voltage applied only intermittently by the voltage generator 14, as needed, to achieve an active chlorine concentration in the desired range (typically around 300 ppm). Recirculation flow rates of around 80 1/hr have been found to provide for adequate regeneration of the active chlorine species at serum concentrations of below 1%.

Optionally, a sensor 26, located in the treatment vessel 22 or in the return line 24, senses a property of the solution, such as hypochlorite concentration, oxidation reduction potential, or pH, which is dependent on the active species. A voltage controller 28 is connected to the sensor and directs the voltage generator 14 to apply a voltage across the electrodes 16 and 18 when the property sensed by the sensor reaches a preselected value corresponding to a preselected minimum level of active species in the solution.

Alternatively, the rate of recirculation of the antimicrobial solution through the generator is adjusted to achieve the desired active chlorine concentration, or recirculation is carried out only intermittently.

The organic material may form a complex with the active chlorine species. The complex is broken down when the depleted solution is recirculated through the generator, thereby liberating the chlorine species again. However, the antimicrobial solution also contains sodium chloride, which is capable of being converted to the active chlorine species when recycled through the generator.

With each pass through the generator, a portion of the sodium chloride is converted to a catholyte which is drawn off from the generator along a fluid line 30. The proportion of the catholyte solution withdrawn is adjusted to maintain the pH of the antimicrobial solution within an optimum range for effective microbe kill. A range of from around pH 2 to 9 is preferred with a particulary prefered pH of 5 to 9. Optionally, an additional quantity of sodium chloride solution is added to the recirculating solution through supply line 12 before it passes through the generator. In particular, when an extensive period of recirculation is desired, such further additions of sodium chloride replenish the sodium chloride concentration.

Preferably, valves 34 and 36 control the passage of sodium chloride and depleted solution, respectively, into the inlet line 12. Optionally, a second inlet line 38 provides for addition of water, to dilute the supply of fresh sodium chloride entering the generator. The system also includes a pump 40 for recirculating the solution. Optionally, the pump is fluidly connected to the return line, although other locations which permit recirculation are also contemplated, such as in the outlet line.

While the system has been described with particular reference to active chlorine solutions derived from brine, it should be appreciated that other sources of the active chlorine species optionally replace, or are used in combination with, the brine solution.

Alternatively, other species which are active as antimicrobials are used, either singly or in combination with the chlorine species. As shown in Table 3, electrochemically activated solutions derived from potassium bromide are effective as sterilants or disinfectants, although kill rates are generally slower than for solutions derived from sodium chloride. The kill rates are expressed in terms of average linear regression D-value (a measure of the time required to reduce the population by 1 log).

TABLE 3

*Bacillus subtilis* D-value Table Using Sodium Chloride and Sodium Bromide Derived Solutions

| Solution | pH of Solution | Temp (° C.) | D-value (sec) | Free Halogen (ppm.) |
|---|---|---|---|---|
| NaCl | 7.52 | 21 | 19.4 | 282 |
| NaCl | 7.64 | 21 | 22.1 | 291 |
| NaCl | 7.84 | 21 | 28.0 | 280 |
| NaCl | 7.71 | 20 | 36.6 | 296 |
| NaBr | 9.43 | 20 | 302.5 | 291 |
| NaBr | 9.45 | 20 | 314.1 | 291 |

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of microbial decontamination of items in the presence of organic load or degraded active oxidizing species, the method comprising:

passing an amount of a halide solution through an electrolytic cell to generate an antimicrobial solution which includes the active oxidizing species;

adjusting the antimicrobial solution to a pH of from 5 to 9;

transporting the antimicrobial solution to a treatment vessel;

immersing items to be microbially decontaminated in the antimicrobial solution; and, returning a portion of the antimicrobial solution with depleted active oxidizing species from the vessel back to the electrolytic cell for generation of a regenerated antimicrobial solution which includes active oxidizing species.

2. The method of claim 1, further including returning the regenerated antimicrobial solution to the treatment vessel.

3. The method of claim 2, wherein the step of returning the portion of the antimicrobial solution to the electrolytic cell and the step of returning the regenerated antimicrobial solution to the treatment vessel are repeated concurrently to define a circulation loop until a preselected concentration of active oxidizing species is obtained in the treatment vessel.

4. The method of claim 3, further including:

adding sodium chloride to the portion of the antimicrobial solution returned to the electrolytic cell.

5. The method of claim 2, further including:

filtering the portion of antimicrobial solution before it is returned to the electrolytic cell.

6. The method of claim 1 wherein the halide is sodium chloride and wherein the active oxidizing species include chlorine species.

7. The method of claim 1 wherein the halide is sodium bromide and wherein the active oxidizing species include bromine species.

8. The method of claim 1, further including continuously recirculating a portion of the antimicrobial solution from the treatment vessel to the electrolytic cell and back to the treatment vessel.

9. The method of claim 8, wherein the antimicrobial solution is continuously recirculated at a flow rate of arond 80/hr.

10. The method of claim 1, wherein the electrolytic cell includes an anode and a cathode and wherein the step of returning the portion of the solution with depleted active oxidizing species includes directing the portion along a fluid flow path which enters the electrolytic cell adjacent the cathode and exits the electrolytic cell adjacent the anode.

11. A method of microbial decontamination of items in the presence of organic load or degraded active oxidizing species, the method comprising:

passing a halide solution through an electrolytic cell to generate an antimicrobial solution which includes the active oxidizing species;

transporting the antimicrobial solution to a treatment vessel;

immersing items to be microbially decontaminated in the antimicrobial solution;

returning a portion of the antimicrobial solution with depleted active oxidizing species from the vessel back to the electrolytic cell to regenerate the active oxidizing species;

sensing a property of the antimicrobial solution which is dependent on a concentration of active oxidizing species; and applying a voltage to the electrolytic cell intermittently to generate active oxidizing species when a preselected minimum concentration of active oxidizing species in the treatment vessel is reached.

12. A method of microbial decontamination of items in the presence of organic load or degraded active oxidizing species, the method comprising:

passing a halide solution through an electrolytic cell to generate an antimicrobial solution which includes the active oxidizing species;

transporting the antimicrobial solution to a treatment vessel;

immersing items to be microbially decontaminated in the antimicrobial solution;

recirculating a portion of the antimicrobial solution from the treatment vessel to the electrolytic cell and back to the treatment vessel to regenerate the active oxidizing species; and controlling at least one of the recirculation, a voltage applied to the electrolytic cell, and addition of a halide species source to the recirculating solution portion to maintain a concentration of free halogen species in the vessel of at least 10 ppm.

13. The method of claim 12, wherein the concentration of free halogen species in the vessel is maintained at least 300 ppm.

14. A method of regeneration of an electrochemically activated antimicrobial solution comprising:

passing an amount of a first solution through an electrolytic cell to generate an antimicrobial solution which includes active oxidizing species;

transporting the antimicrobial solution to a treatment vessel; and immersing items to be microbially decontaminated in the antimicrobial solution;

characterized by:

returning a portion of the antimicrobial solution with depleted active oxidizing species from the vessel back to the electrolytic cell for generation of a regenerated antimicrobial solution which includes active oxidizing species; and applying a voltage to the electrolytic cell intermittently to generate active oxidizing species when a preselected minimum concentration of active oxidizing species in the treatment vessel is reached.

15. The method of claim 14, further characterized by:

continuously recirculating a portion of the antimicrobial solution from the treatment vessel to the electrolytic cell and back to the treatment vessel.

16. The method of claim 14, further characterized by:

the steps of transporting the antimicrobial solution to the treatment vessel and returning the portion of the solution with depleted active oxidizing species from the vessel back to the electrolytic cell are repeated continuously.

17. The method of claim 14, wherein the first solution includes sodium chloride and wherein the active oxidizing species include free chlorine species, the method further characterized by:

the step of returning the portion of the solution with depleted active oxidizing species from the vessel back to the electrolytic cell includes regeneration of an antimicrobial solution including free chlorine species.

18. A system for regeneration of active antimicrobial species comprising:

a source of a salt solution;

an electrolytic cell for generating an antimicrobial solution which includes active antimicrobial species, from the salt solution and from a depleted solution which is depleted of active antimicrobial species;

an inlet line, which fluidly connects the source of the salt solution to the electrolytic cell;

an outlet line, which fluidly connects the electrolytic cell to a treatment vessel for transporting the antimicrobial solution to the vessel;

a return line, which fluidly connects the vessel to the electrolytic cell for returning a portion of the depleted antimicrobial solution to the electrolytic cell for regeneration of active antimicrobial species; and a sensor for detecting a measure of a property of the antimicrobial solution which is dependent on a concentration of active species in the antimicrobial solution.

19. The system of claim 18, further including a pump, fluidly connected to the system, for pumping the depleted solution through the inlet line to the electrolytic cell.

20. The system of claim 18, wherein the pump continuously recirculates the depleted solution through the electrolytic cell.

21. The system of claim 18, wherein the electrolytic cell includes electrodes and wherein the system further includes a voltage generator for applying a voltage across the electrodes.

22. The system of claim 18, wherein the active antimicrobial species includes species from the group consisting of free chlorine species, free bromine species, and combinations thereof.

23. The system of claim 18, wherein the property is concentration of free chlorine species.

24. The system of claim 18, further including a voltage generator for applying a voltage across the electrolytic cell, and a voltage controller for controlling the voltage generator in response to the measure of the property detected by the sensor.

25. The system of claim 18, further including a treatment vessel.

26. A system for regeneration of active antimicrobial species comprising:

a source of a salt solution;

an electrolytic cell for generating an antimicrobial solution which includes active antimicrobial species, from the salt solution and from a depleted solution which is depleted of active antimicrobial species;

an inlet line, which fluidly connects the source of the salt solution to the electrolytic cell;

an outlet line, which fluidly connects the electrolytic cell to a treatment vessel for transporting the antimicrobial solution to the vessel;

a return line, which fluidly connects the vessel to the electrolytic cell for returning a portion of the depleted antimicrobial solution to the electrolytic cell for regeneration of active antimicrobial species; and a valve for controlling addition of the salt solution from the source of salt solution to the electrolytic cell for maintaining a minimum concentration of active antimicrobial species.

* * * * *